United States Patent [19]

Fussell

[11] Patent Number: 5,233,680
[45] Date of Patent: Aug. 3, 1993

[54] WREATH-SHAPED ELECTRICALLY ACTIVATED AROMATIC ORNAMENT

[75] Inventor: David A. Fussell, Stone Mountain, Ga.

[73] Assignee: Ornamotor, Inc., Duluth, Ga.

[21] Appl. No.: 953,738

[22] Filed: Sep. 29, 1992

[51] Int. Cl.$^5$ .................. F24F 6/00; A61M 16/00
[52] U.S. Cl. .................... 392/390; 392/392;
  261/DIG. 65; 239/51.5; 239/55; 428/10;
  428/905
[58] Field of Search ............ 392/390, 392, 393-395;
  261/DIG. 65; 239/51.5, 55-57; 422/4, 124,
  125; 428/10, 905; 362/122; D23/367;
  D117/120

[56] References Cited

U.S. PATENT DOCUMENTS

| | | | |
|---|---|---|---|
| D. 197,770 | 3/1964 | Friedman et al. | D23/367 |
| 3,220,913 | 11/1965 | Thomas | 239/51.5 |
| 3,500,035 | 10/1970 | Franc | 428/10 |
| 3,698,991 | 10/1972 | Susewitz | 428/905 |
| 3,945,568 | 3/1976 | Bychowski | 428/905 |
| 4,745,007 | 5/1988 | Addamiano et al. | 427/249 |
| 4,849,606 | 7/1989 | Martens et al. | 392/390 |
| 4,890,791 | 1/1990 | Hoffman | 239/57 |

FOREIGN PATENT DOCUMENTS 353057 7/1931 United Kingdom ............... 392/393

OTHER PUBLICATIONS

*Fairfax Northern Virginia Sun,* "Victorian Potpourri Wreath" (Advertisement), Jan. 15, 1986, p. 9, Classified Crafts, Dept. C. 22210, Box 159, Bixby Okla. 74008.

*Primary Examiner*—Bruce A. Reynolds
*Assistant Examiner*—John A. Jeffery
*Attorney, Agent, or Firm*—James A. Hinkle

[57] ABSTRACT

An electrically activated aromatic ornament (1, 9, 20, 28 and 29) has a wreath shaped structure in which an electrical heater (2) activates a volatile aromatic material (30) to cause incense gases to be exhausted through selective orifices (22 and 24) proximate decorative objects. Electrical power can be provided through such limited power electrical conductors as Christmas tree light cords (5 and 6) for hanging small sizes of this aromatic ornament on Christmas trees or on other fragile objects. Electrical power can be provided also through standard extension cords (31 and 32) for larger sizes to be hung on larger and more sturdy structures. Decorative items such as natural leaves, flowers, ribbons and artificial plants can be attached to some embodiments of this invention.

24 Claims, 2 Drawing Sheets

WREATH-SHAPED ELECTRICALLY ACTIVATED AROMATIC ORNAMENT

BACKGROUND OF THE INVENTION

I. Field of the Invention

The present invention relates generally to the field of electrically activated aromatic containers and in particular to a hang-up form of wreath shaped ornament having an electrically heated interior into which a volatile aromatic material is placed and having incense orifices through which aromatic gases are exhaustible.

II. Description of the Prior Art

The prior art teaches a wide variety of electrically heated vapor dispensing containers. None, however are in the form of a wreath that can be hung as an ornament such as a Christmas tree ornament, a light fixture ornament or a door ornament for effective and safe dispensing of incense aroma. Nor does any of the prior art teach an incense dispenser onto which natural or artificial decorations can be hung in a wreath form.

Examples of different but related prior art include the following patents. U.S. Pat. No. 4,849,606 describes a tamper resistant container utilizing a flexible seal and having a central ridge to prevent its collapse from pressure of objects inadvertently placed or dropped on it. It was not a hang-up device but instead was a plug-in container that was attached directly to an electrical plug. It could not be hung on a Christmas tree and powered by a Christmas tree light plug. Nor was it an ornament that could be hung as a decorative item. U.S. Pat. No. 4,571,485 disclosed an electrically heated aromatic generator utilizing a replaceable aromatic cube which is inserted into a well in the generator. The aromatic cube is an open ended chimney structure having a shallow box supported at its lower end by means of radial ribs which extended between walls of the cube. A porous pad having acceptable wicking capacity is held within the box and impregnated with a volatile aromatic liquid. The pad is covered with a wire or plastic net which is secured to the box to retain the pad. A peel-off cover can be placed over the net to prevent volatilization of the liquid during prolonged storage of the cube. U.S. Pat. No. 4,383,377 teaches a hot air hand dryer having a housing which includes a perforated container or cup for holding a vaporizable deodorizing material. U.S. Pat. No. 3,990,848 describes a battery operated vapor dispensing device which utilizes a cartridge for holding a vaporizable material. U.S. Pat. No. 4,629,604 describes an aroma cartridge player in which each cartridge holds a plurality of fragrances. The cartridge has a rectangular multi-sectioned framework. The cartridge is inserted into the cartridge player which utilizes heat to vaporize the volatile aromatic materials.

SUMMARY OF THE INVENTION

In accordance with the present invention, it is contemplated that one object of this invention is to provide a decorative ornament in the form of a wreath which contains volatile aromatic material in proximity to an internal electrical heater.

Another object is to provide a decorative ornament in the form of a wreath containing volatile aromatic material in proximity to an internal electrical heater which is powerable through a Christmas tree light wire or similarly limited source of electrical current.

Another object is to provide an incense dispenser wreath ornament which is safe to be hung on a Christmas tree when heated by electrical current from a Christmas tree light cord.

Another object is to provide a hangable and electrically heatable wreath shaped incense dispenser onto which decorative items can be positioned.

Yet another object is to provide a hangable wreath shaped incense dispenser having decorative portions with orifices through which incense gases are discharged from internally positioned aromatic material when heated electrically through an electrical cord.

This invention accomplishes the above and other objectives with an electrically activated aromatic ornament having a wreath shaped structure in which an electrical heater activates a volatile aromatic material to cause incense gases to be exhausted through selective orifices within decorative objects. Electrical power can be provided through such limited power electrical conductors as Christmas tree light cords for hanging small sizes of this aromatic ornament on Christmas trees or on other fragile objects. Electrical power can be provided also through standard extension cords for larger sizes to be hung on larger and more sturdy structures. Decorative items such as natural leaves, flowers, ribbons and artificial plants can be attached to some embodiments of this invention.

Other objects, advantages and capabilities of the invention will become apparent from the following description taken in conjunction with the accompanying drawings showing preferred embodiments of the invention.

DESCRIPTION OF PREFERRED EMBODIMENT

Figure 1:
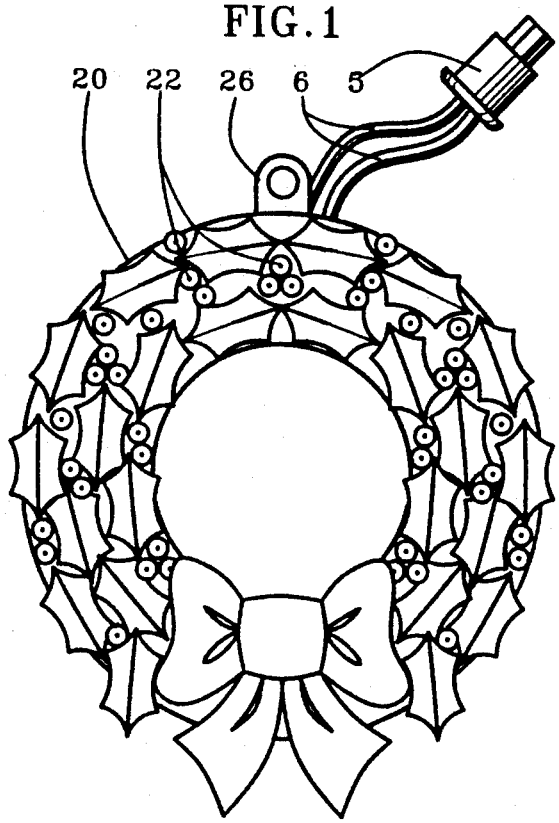
FIG. 1 is a front view of a Christmas tree embodiment of this electrically activated aromatic ornament.

Referring to the drawings wherein like reference numerals designate corresponding parts throughout the several figures, an electrically activated aromatic ornament has a wreath shaped base 1 with an electrical resistance heater 2 embedded in a bottom wall 3 of a fragrance container 4. The electrical resistance heater 2 can be supplied with electrical current through electrical wiring similar to a Christmas tree light plug 5 and wires 6. The fragrance container 4 is a circumferential channel with outside wall 7 and inside wall 8. The fragrance container 4 is coverable by a cover plate 9 having a cover plate sleeve 10 that is positioned inside of the inside wall 8 of the fragrance container 4.

Within the wreath shaped base 1, the inside wall 8 of the fragrance container 4 has inside diameter threading 11. The cover plate sleeve 10 has matching outside diameter threading preferably in the form of outside diameter thread engagement members 12 that are extended radially outward from a circumferential outside diameter 13 of the cover plate sleeve 10. Thread bypass channels 14 in the inside diameter threading 11 allow passage of the outside diameter thread engagement members 12 through the inside diameter threading 11 at designed circumferential positions.

After the outside diameter thread engagement members 12 are inserted through the thread bypass channels 14, the cover plate 9 and the wreath shaped base 1 can be rotated in relationship to each other. This positions the outside diameter thread engagement members 12 at an opposite side of the inside diameter threading 11 from the cover plate 9 to hold the cover plate 9 on top of the walls 7 and 8 of the fragrance container 4.

A thread lock means can be provided for snap locking and snap unlocking. At a common circumferential side of each thread bypass channel 14 is a form of notch 15 into which the thread engagement members 12 are positioned when rotated. Immediately adjacent to the thread bypass channels 14 circumferentially is a notch entrance incline 16 on a notch wall 17 that provides select resistance to rotation of the cover plate 9. The resistance is generated in proportion to bend resistance of the thread engagement members 12 in ascending the notch entrance incline 16 circumferentially. At one side of each notch 15 is a notch abutment 18 which prevents rotation of the thread engagement members 12 past the notch 15. There is a notch exit incline 19 on the opposite side of each notch 15 from the notch abutment 18. The notch exit incline 19 is on an opposite side of the notch wall 17 from the notch entrance incline 16. The notch exit incline 19 allows the thread engagement members 12 to snap into the notch 15. The notch exit incline 19 also requires select rotational resistance to bending moment of the thread engagement members 12 for unlocking rotation in a circumferential direction towards the thread bypass channels 14.

This form of thread locking provides convenient detection by a user of the locking relationship of the threads. Any rotation beyond the thread bypass channels 14 assures a locking of the threads 11 and 12 that is reliable for the use conditions of this electrically activated aromatic ornament.

Components of this thread locking means can have a variety of shapes. Mere indentation in inside diameter threading for an appendage on outside diameter threading at a desired position of rotation is a foreseeable modification of this thread locking means. It would not necessarily employ the thread bypass channel 14.

A wreath shaped ornament structure 20 is attachable to an opposite side of the cover plate 9 from the wreath shaped base 1. An internal fluid conveyance 21 in the wreath shaped ornament structure 20 can be employed to convey aromatic gases from the fragrance container 4 to ornament outlet orifices 22. In the cover plate 9 there can be cover plate orifices 23 which allow passage of aromatic gases from the fragrance container 4 to the internal fluid conveyance 21 in the wreath shaped ornament structure 20.

In addition, or alternatively, to outlet of aromatic or scented gases through the ornament outlet orifices 22, there can be conveyance outlet orifices 24. These are direct outlets in outside walls 7 or at ends of outside walls 7.

Also in addition, or alternatively, to the ornament outlet orifices 22, the cover plate 9 can be separated selectively from the fragrance container 4 by radial spacers 25. This allows escape of the aromatic gases circumferentially from between the cover plate 9 and the wreath shaped base 1.

Either one or any combination of these scent outlet means can be employed. The radial spacers 25 may be the most efficient and conveniently variable in production for different fragrance characteristics. But the ornamental outlet orifices 22 in select ornamental structures can have greater public appeal. A selection for different use conditions is an advantage.

This electrically activated aromatic ornament can be suspended from such structures as Christmas trees, doors and fixtures by a attachment appendage 26 extended preferably from the cover plate 9. This is a balanced position between the base 1 and the ornament 20 which are attached to opposite sides of the cover plate 9. The ornament structure 20 can be glued or otherwise attached to the cover plate 9. The base 1 is attached to the cover plate 9 by means of the sleeve 10 and threading means.

The wreath shaped base 1 can be constructed of a variety of suitably heat conductive and electrical resistance materials, however, polypropylene is preferred. This allows heat to be conveyed through bottom wall 3 from the resistance heater 2 without danger of electrical conveyance from the resistor 2 or wires 6 attached to its opposite terminals. A suitable potting material 27 can be employed to hold the electrical resistance heater 2 in an embedded relationship to the base 1. The potting material 27 is preferably heat resistant and non-conductive of electricity.

The wreath shaped base 1 can have a wide variety of configurations, provided its internal structure is suitable for threading means such as described. It can be hollow but need not be. A wreath shape is intended to include a circle with irregularities for ornaments and with or without a central orifice. It can be constructed in any appropriate size, although Christmas tree ornament size is a major objective. The ornaments can be either attached or attachable.

Figure 5:
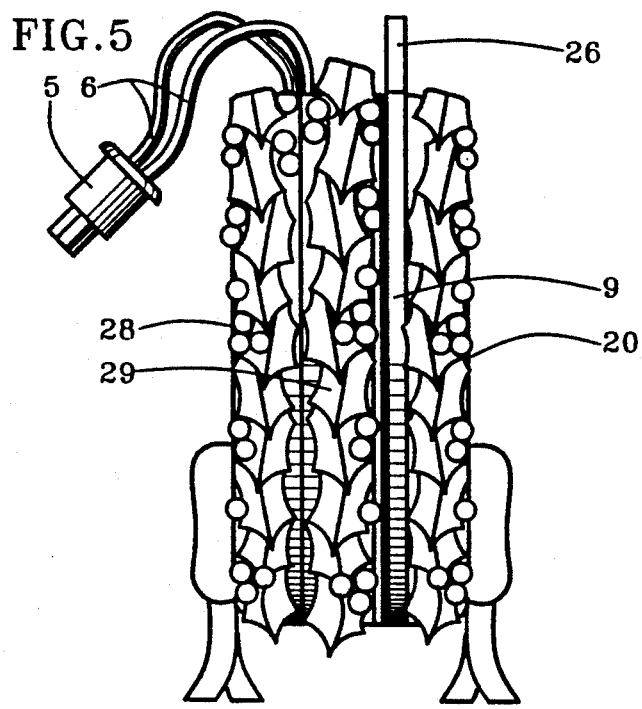
FIG. 5 is a side view of an embodiment with ornamentation on both front and rear and on central sections of this invention.

Referring to FIG. 5, a base side ornament structure 28 and a circumferential ornament structure 29 can be employed. This gives an ornamental appearance from all angles, rather than from the front only. Conveyance 21 and outlets 22 are optional for the base side ornament structure 28. If not employed, the base side ornament structure 28 can be thinner and lighter for better balance.

Figure 6:
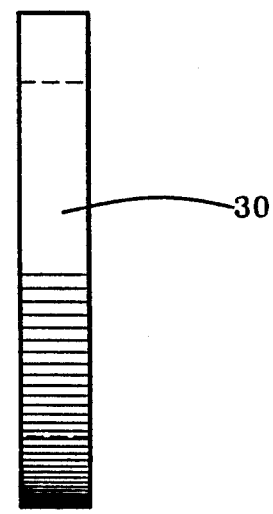
FIG. 6 is a side view of an aromatic cartridge that is positioned in a cartridge container in the base component.

Referring to FIG. 6, a fragrance cartridge 30 can be ring-shaped to fit into the circumferential channel of the fragrance container 9. The fragrance material is preferably volatile in that it changes from a solid directly to a gas without becoming a liquid such as a wax. In this regard, it is different from a fragrance candle that melts into a liquid when heated. Some fragrance containing waxes can be used that give off aromatic gases without melting from the limited heat involved in this invention.

Figure 2:
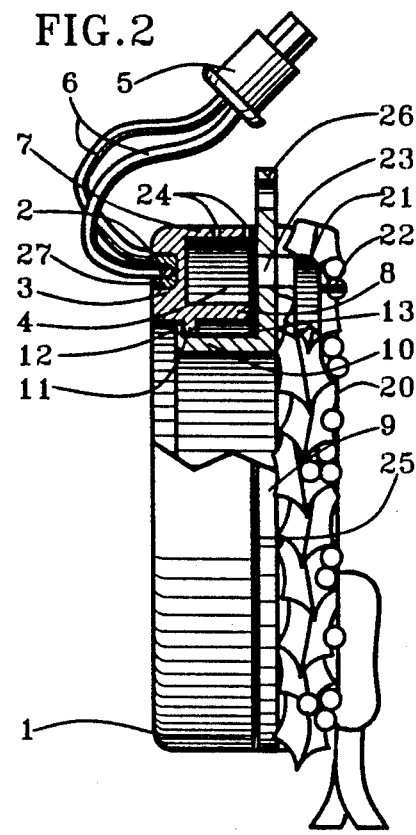
FIG. 2 is a cutaway side view of the FIG. 1 illustration.
Figure 3:
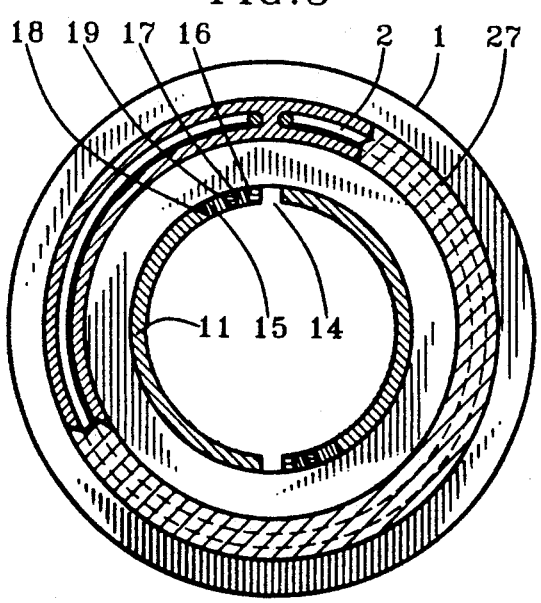
FIG. 3 is a cutaway rear view of a base component in which volatile aromatic material is contained and heated.
Figure 4:
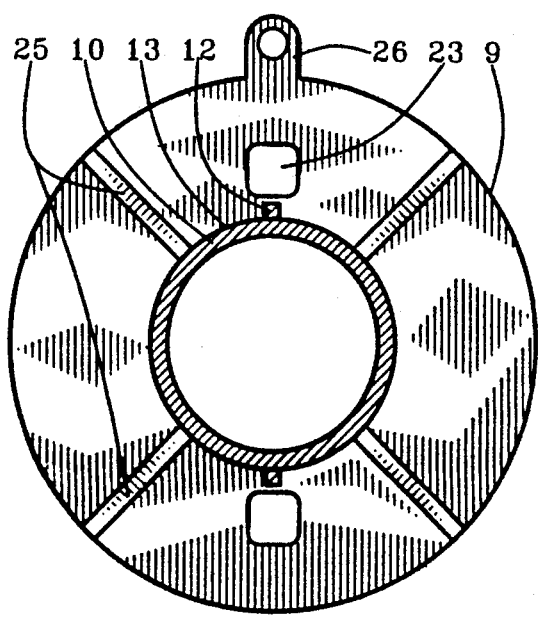
FIG. 4 is an elevation view of a container cover plate.
Figure 7:
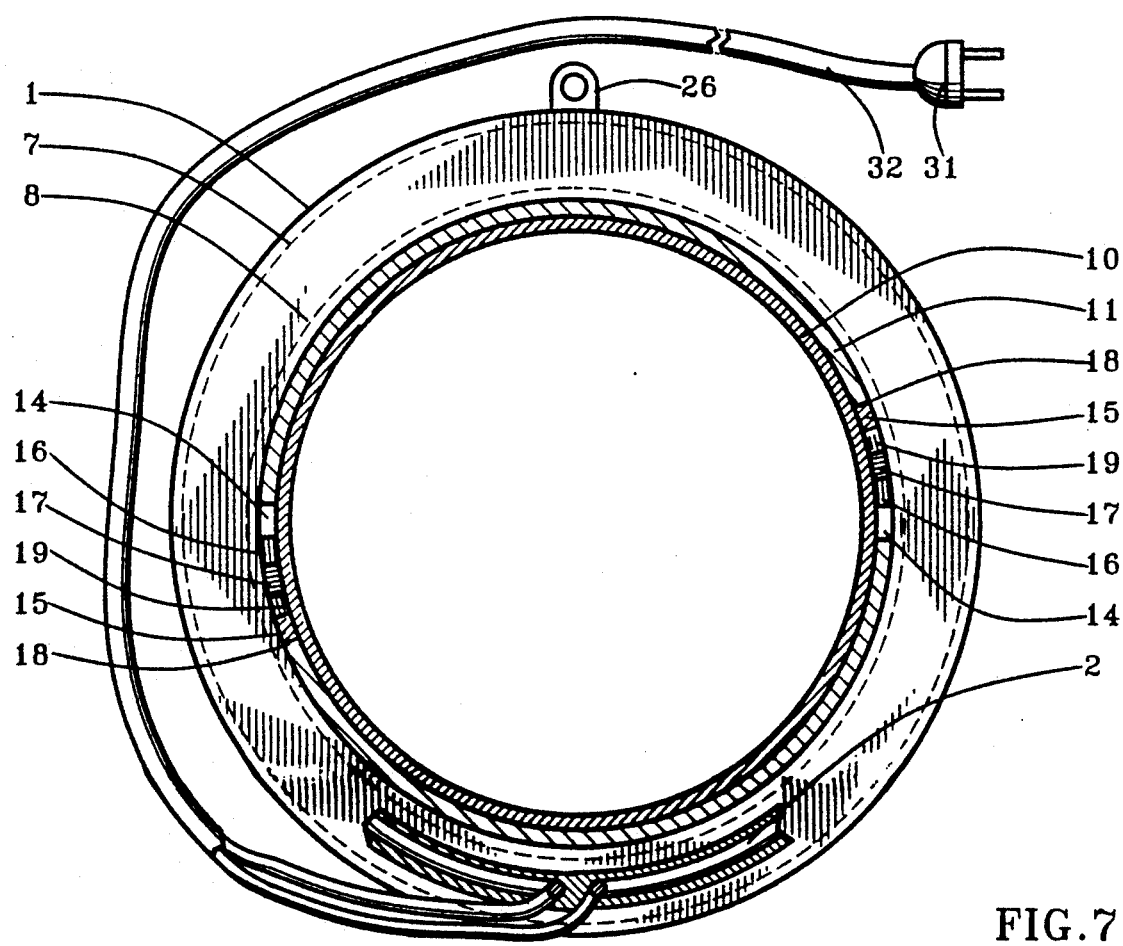
FIG. 7 is a cutaway rear view of a large size of this invention that can be hung on doors, walls and fixtures.

Referring to FIG. 7, a standard electrical plug 31 and electrical cord 32 can be employed with a base 1 having a large diameter. This would allow efficient use of the greater amount of electrical current for a resistance heater 2 to heat a fragrance cartridge 30 having a matching large diameter. Large diameters are preferable for optional attachment of decorative items in addition to the ornamental structure 1 shown in FIGS. 1,2 and 5. Attachable decorative items can be leaves, flowers, berries, ribbons and other items associated with wreaths. For this application, it is foreseeable that this is a figurative ornament intended for attachment of decorative items for some use conditions. Other aspects of this embodiment of the invention are the same as described in relation to FIGS. 1-6.

Various modifications may be made of the invention without departing from the scope thereof and it is desired, therefore, that only such limitations shall be placed thereon as are imposed by the prior art and which are set forth in the appended claims.

What is claimed is:

1. An electrically activated aromatic ornament comprising:
   a wreath shaped base,
   a fragrance container positioned circumferentially in a wall of the wreath shaped base,
   an electrical resistance heater positioned circumferentially proximate the fragrance container,
   a cover plate positioned on an open end of the fragrance container,
   a means for attachment of the cover plate to the wreath shaped base circumferentially internal from the fragrance container,
   a wreath shaped ornament structure attachable to the cover plate, and
   incense conveyance means in communication between the fragrance container and select positions in relation to the electrically activated aromatic ornament.

2. An electrically activated aromatic ornament as claimed in claim 1, wherein the wreath shaped base has a circumferential inside perimeter concentric with a circumferential outside perimeter.

3. An electrically activated aromatic ornament as claimed in claim 2, wherein the cover plate has a circumferential inside perimeter concentric with a circumferential outside perimeter, a cover plate sleeve on the circumferential inside perimeter of the cover plate, and an outside perimeter of the cover plate sleeve that is positioned within the circumferential inside perimeter of the wreath shaped base.

4. An electrically activated aromatic ornament as claimed in claim 3, wherein the means for attachment of the cover plate to the wreath shaped base circumferentially internal from the fragrance container is a mechanical fastener in fastener relationship between the cover plate sleeve and the circumferential inside perimeter of the wreath shaped base.

5. An electrically activated aromatic ornament as claimed in claim 4, wherein the mechanical fastener is comprised of:
   inside diameter threading on the circumferential inside perimeter of the wreath shaped base,
   at least one outside diameter thread engagement member extended radially outward from a circumferential outside perimeter of an end of the cover plate sleeve linearly opposite from the cover plate, and
   at least one thread bypass channel extended linearly from end-to-end of the inside diameter threading on the circumferential inside perimeter of the wreath shaped base in a working relationship in which the at least one outside diameter thread engagement member is slidable through at least one thread bypass channel and then rotatable selectively in thread engagement relationship with the inside diameter threading on the circumferential inside perimeter of the wreath shaped base.

6. An electrically activated aromatic ornament as claimed in claim 5 and further comprising:
   a thread lock means for locking the at least one outside diameter thread engagement member in a select circumferential position of rotation from at least one thread bypass channel.

7. An electrically activated aromatic ornament as claimed in claim 6, wherein the thread lock means is comprised of:
   a notch in the inside diameter threading on the circumferential inside perimeter of the wreath shaped base,
   a notch entrance bevel with a select acute angle on an exterior wall of the notch adjacent to at least one thread bypass channel,
   a notch exit bevel with a select acute angle on an interior wall of the notch adjacent to at least one thread bypass channel,
   distance of at least one outside diameter thread engagement member from an inside surface of the cover plate being proximate a distance of a bottom of the notch from a linear end of an inside wall of the wreath shaped base, and
   at least one outside diameter thread engagement member being selectively resilient such that rotation of the cover plate in a circumferential direction towards the notch causes at least one outside diameter thread engagement member to bend with select resistance to ascend the notch entrance bevel on the exterior wall of the notch adjacent to at least one thread bypass channel to position said one outside diameter thread engagement member in the notch for locking the thread lock means and such that rotation of the cover plate in a circumferential direction towards the said one thread bypass channel causes the said outside diameter thread engagement member to bend with select resistance to ascend the notch exit bevel on the interior wall of the notch adjacent to the said one thread bypass channel for unlocking the thread lock means.

8. An electrically activated aromatic ornament as claimed in claim 4, wherein the mechanical fastener is inside diameter threading in the inside periphery of the wreath shaped base and matching outside diameter threading in the outside periphery of the cover plate sleeve.

9. An electrically activated aromatic ornament as claimed in claim 1, wherein the fragrance container has a circular channel form with opposite walls in the wreath shaped base positioned between an outside perimeter of the wreath shaped base and an inside perimeter of an attachment orifice positioned centrally in the wreath shaped orifice, a channel floor at a linear bottom end of the wreath shaped base, and a channel entrance at a linear top end of the wreath shaped base.

10. An electrically activated aromatic ornament as claimed in claim 9, wherein the wreath shaped base is constructed of a material such as polypropylene which can convey heat while resisting conveyance of electrical current.

11. An electrically activated aromatic ornament as claimed in claim 10, wherein the electrical resistance heater is an electrical resistance member embedded in the channel floor and having a current inlet terminal and a current outlet terminal in juxtaposed relationship at a select circumferential position and further comprising:

select insulating material positioned on the electrical resistance member at a linear bottom of the wreath shaped base.

12. An electrically activated aromatic ornament as claimed in claim 11, wherein the electrical resistance member is constructed of a material having a cross-sectional capacity for generating desired heat from electrical current supplied through electrical conductors similar in current carrying capacity to Christmas tree light wires.

13. An electrically activated aromatic ornament as claimed in claim 12 and further comprising:
 a first Christmas tree light wire in electrical contact with the current inlet terminal,
 a second Christmas tree light wire in electrical contact with the current outlet terminal, and
 a Christmas tree light plug in electrical contact with the first and second Christmas tree light wires.

14. An electrically activated aromatic ornament as claimed in claim 1, wherein the cover plate is constructed of a selectively heat conductive and current resistive material such as polypropylene.

15. An electrically activated aromatic ornament as claimed in claim 1, wherein the wreath shaped base has a circumferential inside perimeter concentric with a circumferential outside perimeter and further comprising:
 a cover plate having a circumferential inside perimeter concentric with a cover plate circumferential outside perimeter on the cover plate,
 a cover plate sleeve on the circumferential inside perimeter of the cover plate,
 an outside perimeter of the cover plate sleeve that is positioned within the circumferential inside perimeter of the wreath shaped base, and
 radial ridges of a select height on a sleeve side of the cover plate for spacing the cover plate a select distance from an open end of the fragrance container to allow release of aromatic gases from heated aromatic material in the fragrance container.

16. An electrically activated aromatic ornament as claimed in claim 1, wherein the wreath shaped base has a circumferential inside perimeter concentric with a circumferential outside perimeter and further comprising:
 a cover plate having a circumferential inside perimeter concentric with a cover plate circumferential outside perimeter on the cover plate,
 a cover plate sleeve on the circumferential inside perimeter of the cover plate,
 an outside perimeter of the cover plate sleeve that is positioned within the circumferential inside perimeter of the wreath shaped base,
 an aromatic gas conveyance in the wreath shaped ornament structure that is attachable to the cover plate,
 at least one aromatic gas outlet orifice in communication with the aromatic gas conveyance positioned selectively in the wreath shaped ornament structure,
 at least one aromatic gas inlet orifice in communication with the aromatic gas conveyance positioned selectively in the wreath shaped ornament structure, and
 at least one aromatic gas conveyance orifice in the container cover plate in aromatic gas communication between the fragrance container and the at least one aromatic gas inlet orifice in the aromatic gas conveyance in the wreath shaped ornament structure.

17. An electrically activated aromatic ornament as claimed in claim 16 and further comprising:
 at least one aromatic outlet orifice in communication directly between an inside periphery and an outside periphery of a wall of the fragrance container in the wreath shaped base.

18. An electrically activated aromatic ornament as claimed in claim 1 and further comprising:
 at least one aromatic outlet orifice in communication directly between an inside periphery and an outside periphery of a wall of the fragrance container in the wreath shaped base.

19. An electrically activated aromatic ornament as claimed in claim 1 and further comprising:
 a wreath shaped ornament structure attachable to the wreath shaped base.

20. An electrically activated aromatic ornament as claimed in claim 19 and further comprising:
 an circumferentially ornamental section positioned between the wreath shaped ornament structure attachable to the cover plate and the wreath shaped ornament structure attachable to the wreath shaped base such that the electrically activated aromatic ornament can be made to appear decorative from all directions.

21. An electrically activated aromatic ornament as claimed in claim 1 and further comprising:
 an attachment appendage extended from an edge of the cover plate.

22. An electrically activated aromatic ornament as claimed in claim 1 and further comprising:
 an attachment appendage extended from an edge of the wreath shaped base.

23. An electrically activated aromatic ornament as claimed in claim 1, wherein the wreath shaped base has a circumferential inside perimeter concentric with a circumferential outside perimeter and further comprising:
 a cover plate having a circumferential inside perimeter concentric with a cover plate circumferential outside perimeter on the cover plate,
 a cover plate sleeve on the circumferential inside perimeter of the cover plate,
 an outside perimeter of the cover plate sleeve that is positioned within the circumferential inside perimeter of the wreath shaped base,
 a radially cross-sectional area of the wreath shaped base, a radially cross-sectional area of the cover plate and a radially cross-sectional area of the wreath shaped ornamental structure attachable to the cover plate being selectively small in proportion to the outside circumferential perimeter of the wreath shaped base, the inside circumferential perimeter of the wreath shaped base, the outside circumferential perimeter of the cover plate, the inside circumferential perimeter of the cover plate, an outside circumferential perimeter of the wreath shaped ornamental structure and an inside circumferential perimeter of the wreath shaped ornamental structure to allow attachment of a select quantity of decorative items.

24. An electrically activated aromatic ornament as claimed in claim 1, wherein the fragrance container has a circular channel form with opposite walls in the wreath shaped base positioned between an outside perimeter of the wreath shaped base and an inside perimeter of an attachment orifice positioned centrally in the wreath shaped orifice, a channel floor at a linear bottom end of the wreath shaped base, and a channel entrance at a linear top end of the wreath shaped base, and further comprising:

a scent cartridge sized and shaped to fit selectively within the opposite walls and channel floor of the circular channel form of the fragrance container.

* * * * *